United States Patent [19]

Madrange et al.

[11] Patent Number: 5,143,518
[45] Date of Patent: Sep. 1, 1992

[54] COSMETIC COMPOSITIONS FOR DYEING AND FOR BLEACHING HAIR

[75] Inventors: Annie Madrange, Saint Germain en Laye; Patrick Canivet, Paris, both of France

[73] Assignee: L'Oreal, Paris, France

[21] Appl. No.: 719,366

[22] Filed: Jun. 24, 1991

Related U.S. Application Data

[63] Continuation of Ser. No. 301,879, Jan. 26, 1989, abandoned, which is a continuation of Ser. No. 37,015, Apr. 10, 1987, abandoned.

[30] Foreign Application Priority Data

Apr. 10, 1986 [FR] France ............... 86 05149

[51] Int. Cl.$^5$ ............................................. A61K 7/13
[52] U.S. Cl. ............................................. 8/405; 8/406; 8/416; 8/421; 424/70
[58] Field of Search ............... 8/405, 406, 416, 421; 424/70

[56] References Cited

U.S. PATENT DOCUMENTS

| | | | |
|---|---|---|---|
| 4,357,141 | 11/1982 | Grollier et al. | 8/406 |
| 4,563,347 | 1/1986 | Starch | 132/200 |
| 4,710,314 | 12/1987 | Madrange et al. | 252/117 |
| 4,820,308 | 4/1989 | Madrange et al. | 8/405 |

FOREIGN PATENT DOCUMENTS

2165550 4/1986 United Kingdom.

*Primary Examiner*—A. Lionel Clingman
*Assistant Examiner*—William S. Parks
*Attorney, Agent, or Firm*—Cushman, Darby & Cushman

[57] ABSTRACT

Composition for dyeing or bleaching hair, to be mixed with an oxidizing solution at the time of use and containing:

(a) a fatty acid soap,
(b) a cationic or amphoteric silicone polymer,
(c) a cationic surface agent,
(d) an alkalifying agent, and
(e) a cationic polymer chosen from quaternary polyammonium polymers, quaternized or unquaternized vinylpyrrolidone/dialkylaminoalkyl acrylate or methacrylate copolymers, poly(methacrylamidopropyltrimethylammonium chloride), cationic proteins and polyaminoamides which may crosslinked or alkylated.

When these compositions are intended for dyeing hair, they also contain oxidation dye precursors and, if desired, couplers, as well as a reducing agent.

This composition, which foams slightly, allows a very easy distribution throughout the hair and it improves the cosmetic properties of the hair, especially its disentangling, and imparts a silky feel thereto.

27 Claims, No Drawings

COSMETIC COMPOSITIONS FOR DYEING AND FOR BLEACHING HAIR

This is a continuation of application Ser. No. 07/301,879, filed Jan. 26, 1989, now abandoned, which is a continuation of application Ser. No. 07/037,015, filed Apr. 10, 1987, now abandoned.

The present invention relates to new cosmetic compositions for dyeing or for bleaching hair, to be diluted with an oxidizing solution at the time of use, and to their application to hair.

In the present technique for dyeing hair, called "permanent dyeing", oxidation dye precursors dissolved in a substrate with a basic pH and containing a reducing agent are used, these dye precursors being converted into dyes in the hair by condensation in the presence of an oxidizing agent which generally consists of hydrogen peroxide, the oxidizing agent being added to the substrate just before the application to hair.

In the technique for slight bleaching or lightening of hair, an ammoniacal oxidizing composition prepared just before use by mixing the oxidizing agent with an ammoniacal substrate is employed. In the case where it is desired to obtain a higher degree of bleaching, a persalt which generally consists of an alkali metal persulphate is added to the ammoniacal oxidizing composition, just before use in this case as well.

The compositions for dyeing or for bleaching hair, also called dyeing or bleaching substrate, are generally in the form of creams, shampoos or gels.

Dyeing compositions or substrates which contain at least one fatty acid, at least one particular cationic polymer of the quaternary ammonium polymer type, benzyl alcohol and an alkalizing agent have already been proposed in French Patent No. 2,402,446. This dyeing substrate is in form of a stiff gelified cream which adheres well to hair and makes the hair easy to disentangle and pleasant to touch.

However, because of its consistency, this substrate is sometimes difficult to spread throughout the hair, from roots to tips.

The applicants have discovered that the dyeing or bleaching substrate defined below, which is slightly foamy, enables the composition to be spread very easily throughout the hair, by first restricting it to the undyed roots and then by spreading it easily up to the tips; additionally, this composition significantly improves the cosmetic properties of hair and especially the disentangling of wet and dried hair, which acquires a very silky touch.

Therefore, the subject of the invention is a cosmetic composition for dyeing or for bleaching hair, a composition which remains stable during storage and is slightly foamy, to be diluted with an oxidizing solution, containing in an aqueous medium at least one fatty acid soap, at least one cationic or amphoteric silicone polymer at least one cationic surfactant, at least one alkalizing agent and at least one cationic polymer chosen from amongst quaternary polyammonium polymers or "ionenes", vinylpyrrolidonedialkylaminoalkyl acrylate or methacrylate copolymers (quaternized or otherwise), poly(methacrylamidopropyltrimethylammonium chloride) cationic proteins and polyaminoamides which may be crosslinked or alkylated, if required.

When the substrate is used in a dyeing composition, oxidation dye precursors and a reducing agent are added thereto, and in this case a polymer chosen from the group of cationic cyclopolymers may also be used as the cationic polymer.

The soaps used according to the invention are chosen from among alkali metal salts and alkanolamine salts (such as monoethanolamine, diethanolamine, triethanolamine, 2-amino-2-methyl-1-propanol, 2-amino-2-methyl-1,3-propanediol and triisopropanolamine) of $C_{12}$–$C_{18}$ fatty acids, the fatty chain of which is saturated or unsaturated. Among fatty acids, lauric, palmitic, oleic and myristic acids may more particularly be mentioned.

Triethanolamine, monoethanolamine and 2-amino-2-methyl-1-propanol salts of lauric, palmitic and oleic acids are the particularly preferred soaps.

The cationic or amphoteric silicone polymers used according to the invention are polysiloxanes in which one or more of the silicon atoms on the chain carry (carries) an aliphatic amino group, the amine group of which is primary, secondary, tertiary, quaternary or has the betaine structure. The term "aliphatic amino" covers the aminoalkyl and aminohydroxyalkyl radicals, the alkyl chain of which may be interrupted by one or more nitrogen or oxygen atoms.

Cationic silicone polymers are described especially in the CTFA dictionary (3rd edition, 1982, published by The Cosmetic, Toiletry and Fragrance Association, Inc.).

Among the preferred cationic silicone polymers, there may be mentioned the polymer corresponding to the formula:

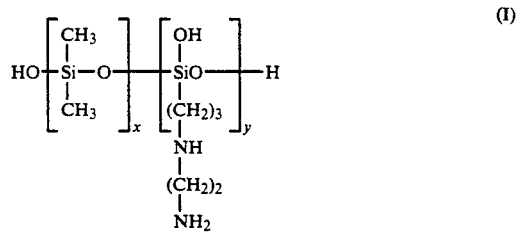

(I)

in which x and y are integers which depend on the molecular weight, the average molecular weight being approximately between 5,000 and 10,000. This polymer is also called "amodimethicone".

Other cationic silicone polymers which can be used according to the invention correspond to the formula:

(II)

in which G is chosen from the group consisting of hydrogen, phenyl, OH, $C_1$–$C_8$ alkyl and preferably methyl;

a denotes 0 or an integer from 1 to 3 and preferably equals 0;

b denotes 0 or 1 and preferably equals 1;

the sum n+m is a number from 1 to 2,000 and preferably from 50 to 150;

n denotes a number from 0 to 1,999 and preferably from 49 to 149 and m denotes an integer from 1 to 2,000 and preferably from 1 to 10; and $R_1$ is a monovalent radical of formula $C_qH_{2q}L$ in which q is an integer from 2 to 8 and L is chosen from amongst the groups:

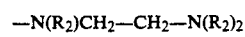

—N(R$_2$)$_2$

—$^{\oplus}$N(R$_2$)$_3$ A$^{\ominus}$

—$^{\oplus}$N(R$_2$)H$_2$ A$^{\ominus}$

—N(R$_2$)CH$_2$—CH$_2$—$^{\oplus}$NR$_2$H$_2$ A$^{\ominus}$ in which R$_2$ is chosen from the group consisting of hydrogen, phenyl, benzyl, a saturated hydrocarbon radical, preferably an alkyl radical containing from 1 to 20 carbon atoms, and A$^{\ominus}$ represents a halide ion.

These compounds are described in greater detail in European Patent Application EP 95,238.

A particularly preferred polymer corresponding to this formula is the polymer called "trimethylsilylamodimethicone" of formula:

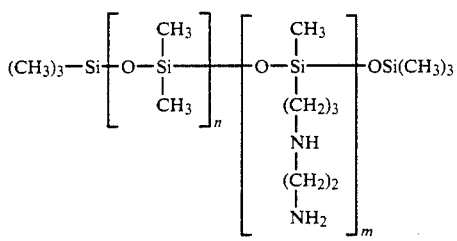

m and n having the same signification as in formula (II)

Other cationic silicone polymers which may be used according to the formula:

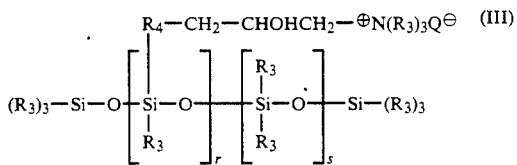

in which R$_3$ denotes a monovalent hydrocarbon radical containing from 1 to 18 carbon atoms and more particularly an alkyl or alkenyl radical such as methyl:

R$_4$ denotes a hydrocarbon radical optionally containing a chain oxygen atom such as, preferably, a C$_1$–C$_{18}$ alkylene radical or a C$_1$–C$_{18}$, and preferably C$_1$–C$_8$, alkyleneoxy radical;

Q$^{\ominus}$ is a halide ion, preferably chloride;

r represents a statistical mean value from 2 to 20 and preferably from 2 to 8; and s represents a statistical mean value from 20 to 200 and preferably from 20 to 50.

These compounds are described in greater detail in U.S. Pat. No. 4,185,087.

A particularly preferred polymer of this class is that sold by Union Carbide under the name "Ucar Silicone ALE 56".

It is also possible to use the cationic silicone polymer of formula:

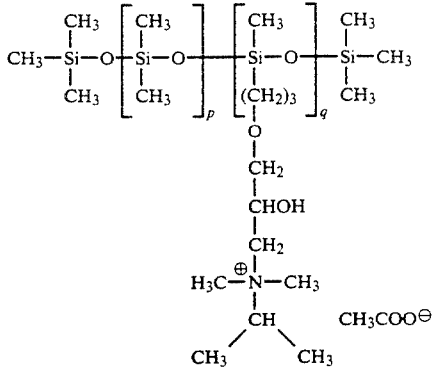

sold under the trade name Abil 9905 by Goldschmidt and the amphoteric silicone polymer of formula:

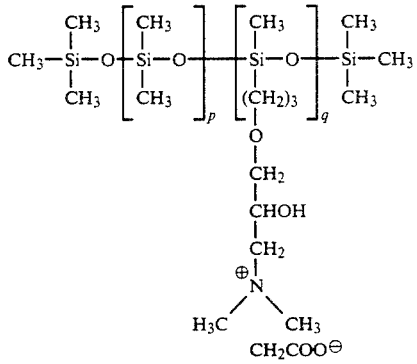

In the above two formulae p and q are integers which depend on the molecular weight, the average molecular weight being comprised between 1000 and 8000. sold under the trade name Abil 9950 by Goldschmidt.

The cationic surfactants used according to the invention correspond to formula (IV):

in which:

(1) R$_5$ and R$_6$ denote methyl, it being possible, in this case, for R$_7$ and R$_8$ to have the following meanings:

i) R$_7$ and R$_8$ denote a straight-chain aliphatic radical, preferably an alkyl radical containing from 12 to 22 carbon atoms, an aliphatic radical derived from tallow fatty acids, containing from 14 to 22 carbon atoms, ii) or R$_7$ denotes a straight-chain aliphatic radical and preferably an alkyl radical containing from 14 to 22 carbon atoms and R$_8$ denotes methyl or benzyl, iii) or R$_7$ denotes an alkylamidopropyl (C$_{14}$–C$_{22}$ alkyl) radical and R$_8$ denotes an alkylacetate (C$_{12}$–C$_{16}$ alkyl) group, iv) or R$_7$ denotes a $\gamma$-gluconamidopropyl radical or an aliphatic radical derived from tallow fatty acids or a C$_{16}$–C$_{18}$ alkyl radical and R$_8$ denotes a hydroxyethyl radical and X$^{\ominus}$ denotes an anion such as a halide or methosulphate ion;

(2) $R_5$ denotes an alkylamidoethyl and/or alkenylamidoethyl group in which the alkyl or alkenyl radical containing from 14 to 22 carbon atoms is derived from tallow fatty acids and $R_6$ and $R_7$ form, with the nitrogen atom, a 2-alkyl(derived from tallow fatty acids)-4,5-dihydroimidazole heterocyclic ring, $R_8$ denotes methyl and
$X^\ominus$ denotes a methosulphate ion; and
(3) $R_5$, $R_6$ and $R_7$ form a six membered aromatic heterocyclic zing with the nitrogen atom and $R_8$ denotes a $C_{14}$-$C_{18}$ alkyl radical and $X^\ominus$ denotes a halide anion.

Among the preferred cationic sufactants, there may be mentioned: dimethylalkyl($C_{18}$)ammonium chloride sold under the name "Genamine DSAC" by Hoechst, trimethylalkyl($C_{20}$-$C_{22}$)ammonium chloride sold under the trade name "Genamine KDM-F" by Hoechst, cetylpyridinium chloride, dimethyldialkyl($C_{12}$-$C_{14}$)ammonium chloride, dimethyl-γ-gluconamidopropylhydroxyethylammonium chloride sold under the name "Ceraphyl 60" by Van Dyk, dimethyldicetylammonium chloride sold under the trade name "Noramium M2 SH", dimethyl dilauryl ammonium chloride sold under the trade name "Noramium M2 CD", dimethylhydroxyethylalkyl(tallow)ammonium chloride, dimethyl dialkyl (hydrogenated tallow)ammonium chloride sold under the trade name "ARQUAT 2H 75, dimethylhydroxyethylcetylammonium chloride and dimethylstearylbenzylammonium sold under the trade names "Ammonyx 4002" by Onyx or "Catigene CS 40" by Stepan. The cationic polymers used according to the invention are chosen from amongst:
1) quaternary ammonium polymers which consist of recurring repeat units of formula (V):

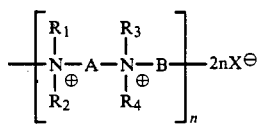

(V)

in which $R_1$, $R_2$, $R_3$ and $R_4$, which may identical or different, represent aliphatic, alicyclic or arylaliphatic radicals containing from 1 to 20 carbon atoms or $C_{1-6}$ and preferably $C_{1-4}$ hydroxyaliphatic radicals,
or $R_1$ and $R_2$ and $R_3$ and $R_4$ together or separately form, with the nitrogen atoms to which they are attached, heterocyclic rings containing, where appropriate, a second heteroatom other than nitrogen,
or, $R_1$, $R_2$, $R_3$ and $R_4$ represent a straight-chain or branched $C_2$-$C_6$ alkyl group substituted with a nitrile, ester, acyl or amide group or with a group

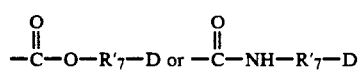

$R'_7$ denoting alkylene and
D denoting a quaternary ammonium group.

A and B may represent polymethylene groups containing from 2 to 20 carbon atoms, it being possible for these groups to be straight-chain or branched, saturated or unsaturated and it being possible for them to contain, inserted n the main chain, one or more aromatic rings or one or more oxygen or sulphur atoms, one or more sulphoxide, sulphone, disulphide, amine, alkylamine, quaternary ammonium, hydroxyl, ureido, amide or ester groups; or A, $R_1$ and $R_3$ form, with the two nitrogen atoms to which they are attached, a piperazine ring.

$X^\ominus$ is an anion derived from an inorganic or organic acid.

n is such that the molecular mass is between 1,000 and 100,000.

Polymers of this type are described, in particular, in French Patents 2,320,330, 2,270,846 and 2,316,271.

Polymers described in French Patent 2,320,330 at pages 4-6 thereof are ionene polymers represented by the formula

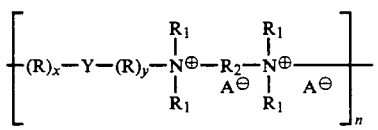

wherein R represents $CH_2$ and/or substituted $CH_2$ group wherein one of the hydrogen atoms is substituted by an alkyl or hydroxymethyl group;
Y is chosen from:

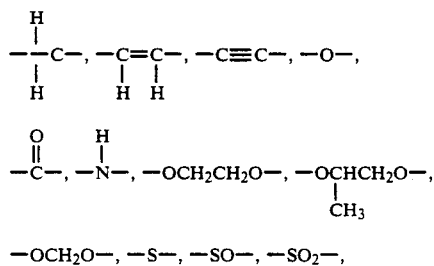

$-OCH_2O-$, $-S-$, $-SO-$, $-SO_2-$, and aryl;
R' represents the group:

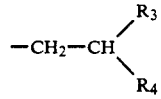

wherein $R_3$ is hydrogen, halogen, alkyl, cycloalky, aryl, alkaryl or aralkyl and $R_4$ is a group chosen from

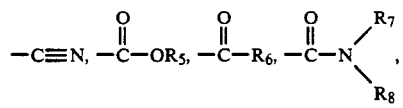

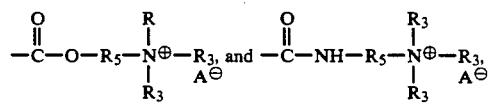

wherein $R_3$ has the same meaning given above;
$R_5$ is selected from alkyl, cycloalkyl and alkoxyalkyl groups;
$R_6$ has the same meaning as $R_5$ or it may represent an aryl group;
$R_7$ and $R_8$ are independently selected from hydrogen and from alkyl, cycloalkyl, aryl, alkaryl, aralkyl and alkoxyalkyl groups;
$R_2$ is a straight or branched chain alkyl having 1 to 18 carbon atoms which may be interrupted by one or several oxygen or sulphur atoms; or it is an aralkyl or cycloalkyl group;

$A^{\ominus}$ is an anion; and x and y are whole numbers from 1 to 10; n is a whole number.

Polymers described in French patent 2,270,846 at pages 1 and 2 are quaternized polymers consisting of recurring units of formula I:

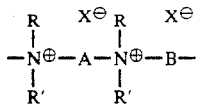     (I)

wherein:

$X^{\ominus}$ represents an anion derived from a mineral or organic acid;

R is a lower alkyl group or a —CH$_2$—CH$_2$—OH group;

R' is an aliphatic, alicyclic or arylaliphatic radical such that R' contains at most 20 carbon atoms; or R and R' attached to the same nitrogen atom form a ring which may contain a second heteroatom other than nitrogen;

A represents a divalent group of the formula

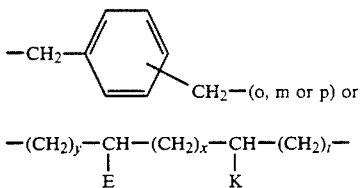

wherein x, y and t are whole numbers from 0 to 11 and such that the sum (x+Y+t) is greater than or equal to 0 and lower than 18 and E and K represent hydrogen or an aliphatic radical having less than 18 carbon atoms or A represents a divalent group of the formulae:

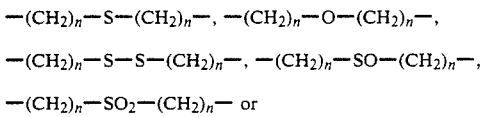

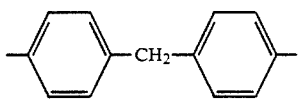

n is a whole number equal to 2 or 3;

B represents a divalent group of the formulae:

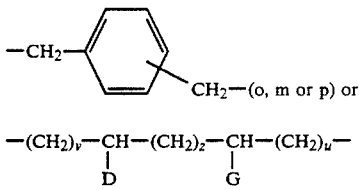

wherein D and G represent a hydrogen atom or an aliphatic radical having less than 18 carbon atoms, and v, z and u are whole numbers which may vary from 0 to 11, two of them may simultaneously be equal to 0, such that the sum (v+z+u) is greater than or equal to 1 and lower than 18 and such that the sum (v+z+u) is greater than 1 when the sum (x+y+t) is equal to 0, or B represents a divalent group of the formulae:

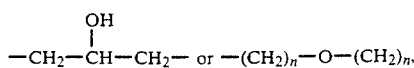

n being as mentioned above.

Polymers described in French patent 2,316,271 at pages 1 and 2 comprise the following recurring units:

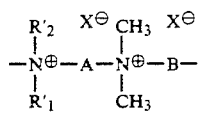     (I)

wherein $X^{\ominus}$ represents an anion derived from an organic or mineral acid;

R'$_2$ is an aliphatic radical having at most 20 carbon atoms;

R'$_1$ is an aliphatic radical, an alicyclic radical or an arylaliphatic radical containing at most 20 and at least 2 carbon atoms, or R'$_1$ and R'$_2$ attached to the same nitrogen atom form a ring which may contain a second heteroatom other than nitrogen;

A represents a divalent group of the formula:

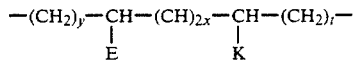

wherein x, y and t are whole numbers from 0 to 11 such that the sum (x+y+t) is greater than or equal to 0 and lower than 18 and E and K represent a hydrogen atom or an aliphatic radical having less than 18 carbon atoms;

B represents a divalent group of the formulae:

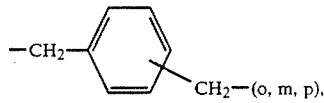

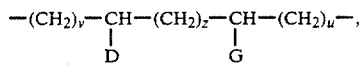

D and G represent a hydrogen atom, an aliphatic radical having less than 18 carbon atoms, v, z and u are whole numbers from 0 to 11, two of them may simultaneously be equal to 0, and such that the sum (v+z+u) is greater than or equal to 1 and lower than 18, such that the sum (v+z+u) is greater than 1 when the sum (x+y+t) is equal to 0, and n is a number equal to 2 or 3 polymers of this type are also described in U.S. Pat. Nos. 2,273,780, 2,375,853, 2,388,614, 2,454,547, 3,206,462, 2,261,002, and 2,271,378; these patents are incorporated by way of reference in the present application.

Other polymers of this type are described in U.S. Pat. Nos. 3,874,870, 4,001,432, 3,929,990, 3,966,904 and 4,005,193, which are also incorporated in the present description by way of reference.

The following polymers are preferred:

1) polymers chosen from the group consisting of polymers which contain one of the following repeat units:

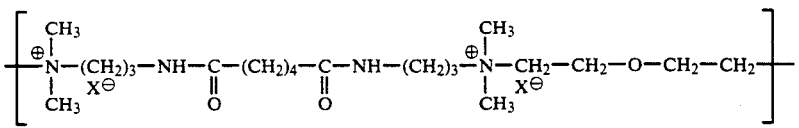

(G₁)

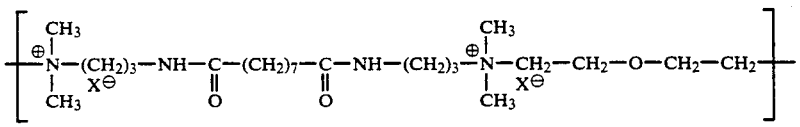

in which X denotes halogen, sold under the trade name "Mirapol AD1" by Miranol, or:

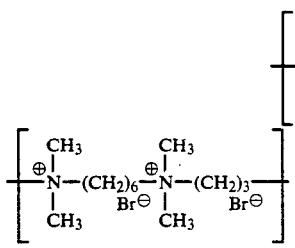

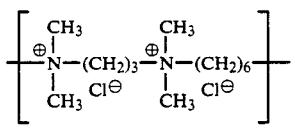 (G₂)

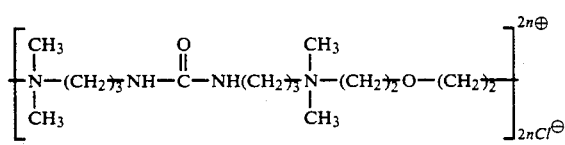

in which n is equal to approximately 6 and which is sold under the name "Mirapol A 15" by Miranol; and poly(dimethylbutenylammonium chloride)-α,ω-bis(-triethanolammonium chloride) sold under the trade name "Onamer M" by Onyx Chemical.

2) Quaternary ammonium polymers consisting of repeat units of formula (VI):

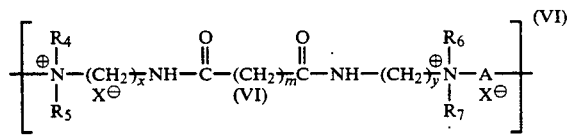

in which
$R_4$, $R_5$, $R_6$ and $R_7$, which may be identical or different, represent a hydrogen atom, a methyl, ethyl, propyl, 2-hydroxyethyl or 2-hydroxypropyl radical or the group —CH₂—CH₂—(O—CH₂—CH₂)$_p$OH in which p is 0 or an integer from 1 to 6, on condition that the radicals $R_4$, $R_5$, $R_6$ and $R_7$ do not simultaneously denote a hydrogen atom,
x and y, which may be identical or different, are integers from 1 to 6,
m is 0 or an integer from 1 to 34,
X is a halogen atom and
A is a divalent group optionally interrupted by an oxygen atom and preferably represents the radical

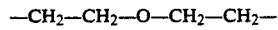

These compounds are described in European Patent 122,324.

The quaternary ammonium polymers which are particularly preferred are those which contain either of the following repeat units:

in which X denotes halogen, sold under the trade name "Mirapol AZ1" by Miranol.

3) Poly(methacrylamidopropyltrimethylammonium chloride) sold under the trade name "Polymaptac" by Texaco Chemicals.

4) Vinylpyrrolidonedialkylaminoalkyl acrylate or methacrylate copolymers (quaternized or otherwise), such as those sold under the trade names "Gafquat" by GAF Corporation, such as, for example, "copolymer 845" and "Gafquat 734 or 755" which are described especially in greater detail in French Patent 2,077,143 and French Patent 2,393,573.

5) Cationic proteins which are chemically modified polypeptides which contain, either at the end of the chain or grafted onto the chain, amine or quaternary ammonium groups. Among these proteins, there may be mentioned, in particular:

collagen hydrolysates containing triethylammonium groups, such as the products sold under the trade name "Quat-Pro E" by Maybrook and called "Triethonium Hydrolyzed Collagen Ethosulphate" in the CTFA dictionary (CTFA is the abbreviation for The Cosmetic, Toiletry and Fragrance Association Inc., 1110 Vermont Avenue N.W. Washington D.C. 20005 U.S.A., who publish the "Cosmetic Ingredient Dictionary" 3rd edition);

collagen hydrolysates which contain trimethylammonium or trimethylstearylammonium chloride groups sold under the trade name "Quat-Pro S" by Maybrook and called "Steartrimonium Hydrolyzed Collagen" in the CTFA dictionary;

hydrolysates of animal proteins, which contain trimethylbenzylammonium groups, such as the products sold under the trade name "Crotein BTA" by Croda and called "Benzyltrimonium hydrolyzed animal protein" in the CTFA dictionary;

protein hydrolysates which contain, on the polypeptide chain, quaternary ammonium groups containing at least one alkyl radical containing from 1 to 18 carbon atoms.

Among these protein hydrolysates, there may be mentioned, among others:

Croquat L, the polypeptide chain of which has an average molecular weight of approximately 2,500 and the quaternary ammonium group of which contains a $C_{12}$ alkyl group;

Croquat M, the polypeptide chain of which has an average molecular weight of approximately 2,500 and the quaternary ammonium group of which contains a $C_{10}$–$C_{18}$ alkyl group;

Croquat S, the polypeptide chain of which has an average molecular weight of approximately 2,700 and the quaternary ammonium group of which contains a $C_{18}$ alkyl group; and Crotein Q, the polypeptide chain of which has an average molecular weight of the order of 12,000 and the quaternary ammonium group of which contains at least one alkyl group containing from 1 to 18 carbon atoms.

These different products are sold by Croda.

Other quaternized proteins are those corresponding to the formula:

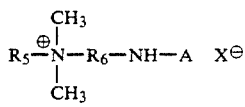

in which A denotes a protein residue derived from collagen protein hydrolysates, $R_5$ denotes a lipophilic group containing up to 30 carbon atoms, $R_6$ represents an alkylene group containing 1 to 6 carbon atoms, and $X^\ominus$ is an anion; these proteins have a molecular weight between 1,500 and 10,000, preferably between 2,000 and 5,000. The preferred product is that sold under the trade name "Lexein QX 3000" by Inolex and called "Cocotrimonium Collagen Hydrolysate" in the CTFA dictionary.

There can also be mentioned hydrolysates of animal proteins, which contain dimethylamine groups, sold under the trade name "Lexein CP 125" by Inolex and referred to under the name "Oleamidopropyl dimethylamine hydrolyzed animal protein" in the CTFA dictionary.

6) Water soluble polyaminoamides, prepared by the polycondensation of an acid compound with a polyamine. These polyaminoamides may be crosslinked and alkylated. Such polymers are described in French Patents 2,252,840 and 2,368,508.

Other polyaminoamides resulting from the condensation of polyalkylenepolyamines with polycarboxylic acids and are alkylated with difunctional agents may be used. There may be mentioned, for example, adipic acid/dialkylaminohydroxyalkyl/dialkylenetriamine polymers in which the alkyl radical contains from 1 to 4 carbon atoms. Such polymers are described in French Patent 1,583,363.

Among these derivatives, adipic acid/dimethylaminohydroxypropyl/diethylenetriamine polymers, sold under the trade names "Cartaretine F, F4 or F8" by Sandoz, may more particularly be mentioned.

There may also be mentioned polyaminoamides obtained by the reaction of a polyalkylenepolyamine containing two primary amine groups and at least one secondary amine group with a dicarboxylic acid, the molar ratio of the polyalkylenepolyamine to the dicarboxylic acid being between 0.8:1 and 1.4:1, the polyaminoamide resulting therefrom being made to react with epichlorohydrin, the molar ratio of epichlorohydrin to the secondary amine groups of the polyamide being between 0.5:1 and 1.8:1. Such polymers are described, in particular, in U.S. Pat. Nos. 3,227,615 and 2,961,347.

A group of polymers which may used advantageously in the dye compositions comprising oxidation dye precursors and a reducing agent consists of: the cyclopolymers with a molecular weight of 20,000 to 3,000,000 and comprising units corresponding to the formulae (VII) or (VIII) below:

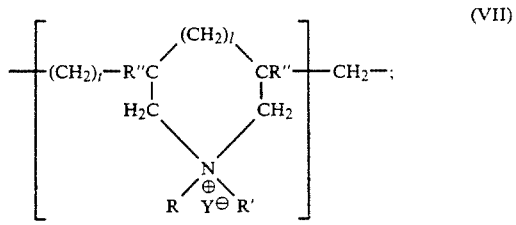

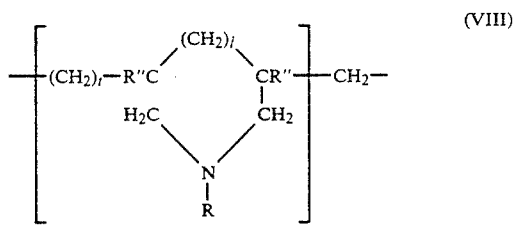

in which l and t are equal to 0 or 1 and the sum (l+t) is equal to 1, R″ denotes hydrogen or methyl, R and R′ denote, independently of each other, an alkyl group containing from 1 to 22 carbon atoms, a hydroxyalkyl group in which the alkyl group preferably has 1 to 5 carbon atoms, or a lower amidoalkyl group and where R and R′ may form, together with the nitrogen atom to which they are linked, heterocyclic groups such as piperidyl or morpholinyl, as well as copolymers comprising in addition to the units of formula (VII) or (VIII) units derived from acrylamide or from diacetoneacrylamide, and $Y^-$ denotes an anion such as bromide, chloride, acetate, borate, citrate, tartrate, bisulphate, bisulphite, sulphate or phosphate.

Among the cyclopolymers defined above, those more particularly preferred are the homopolymer of dimethyldiallylammonium chloride sold by Merck under the trade name "Merquat 100" which has a molecular weight of less than 100,000, and the copolymer of dimethyldiallylammonium chloride with acrylamide which has a molecular weight of more than 500,000 and is sold under the trade name of "Merquat 550" by Merck.

The alkalizing agents used in accordance with the invention may be sodium or potassium hydroxide, aqueous ammonia, and alkanolamines such as those used to form the soap. These alkalizing agents are used in sufficient quantity for the pH of the substrate to be higher than 7 and preferably higher than 8. Aqueous ammonia is preferably used.

When the substrate is employed in a dye composition, it additionally contains oxidation dye precursors and at least one reducing agent. The reducing agents are chosen from thioglycolic acid, thiolactic acid, ammonium thiolactate and sodium metabisulphite. They are used in concentrations of between 0.5 and 2% by weight.

The oxidation dye precursors are aromatic compounds of the diamine, aminophenol or phenol type.

Among these oxidation dyes there may be distinguished, on the one hand, the bases which are para or ortho derivatives chosen from diamines and mono- or diaminophenols and, on the other hand, compounds which are known as modifiers or couplers which are meta derivatives chosen from meta-diamines, meta-aminophenols, phenols and polyphenols.

As para-phenylenediamines which can be used in the compositions according to the invention, there may be mentioned primary, secondary and tertiary para-phenylenediamines, optionally substituted on the benzene ring and preferably those denoted by the general formula:

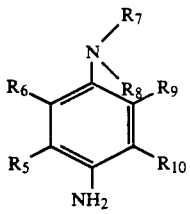

in which:

$R_7$ and $R_8$, which are identical or different, denote a hydrogen atom, a straight-chain or branched lower alkyl group, mono- or polyhydroxylated alkyl, or piperidinoalkyl, carbamylalkyl, dialkylcarbamylalkyl, aminoalkyl, monoalkylaminoalkyl, dialkylaminoalkyl, omega-aminosulphonylalkyl, carboxyalkyl, alkylsulphonamidoalkyl, arylsulphonamidoalkyl, morpholinoalkyl, acylaminoalkyl, sulphoalkyl or alkoxyalkyl group, in which groups the alkyl radical preferably contains 1 to 4 carbon atoms, or $R_7$ and $R_8$ may also form, together with the nitrogen atom, a heterocyclic group containing 5 or 6 ring members, such as morpholine or piperidine;

$R_5$, $R_6$, $R_9$ and $R_{10}$ each denote, independently of each other, a hydrogen or halogen atom, a lower alkyl group preferably containing 1 to 4 carbon atoms, or an —OZ group, Z being a hydroxyalkyl, alkoxyalkyl, acylaminoalkyl, carbalkoxyaminoalkyl, mesylaminoalkyl, ureidoalkyl, aminoalkyl or mono- or dialkylaminoalkyl group.

In the above definition, halogen may mean fluorine, bromine or, preferably, chlorine.

These p-phenylenediamines may be introduced into the dye composition in the form of free base or in salt form, for example in the form of hydrochloride, hydrobromide, sulphate or tartrate.

Among other oxidation bases there may be mentioned p-aminophenol and its homologues in which the aromatic nucleus is substituted by methyl radicals or by chlorine atoms, N-methyl-p-aminophenol, heterocyclic compounds derived from piperidine or from benzomorpholine, 5-aminoindole, ortho-aminophenol, p-aminodiphenylamine, orthophenylenediamines and their substituted derivatives. The oxidation bases are used in concentrations of between 0.01 and 5%.

The dyeing compositions which are the subject of the present application may contain couplers, in addition to one or more oxidation bases. The couplers which may be used in the compositions according to the invention correspond to the general formula:

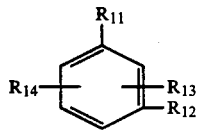

in which:

$R_{11}$ and $R_{12}$, which are identical or different, denote a hydroxyl group, —NHR, where R may be a hydrogen atom, an acyl, ureido, carbalkoxy, carbamylalkyl, alkyl, dialkylcarbamylalkyl, hydroxyalkyl or mesylaminoalkyl group; $R_{11}$ and $R_{12}$ may also denote a hydrogen atom or an alkoxy or alkyl group, provided that at least one of the substituents $R_{11}$ and $R_{12}$ denotes an OH group.

$R_{13}$ and $R_{14}$ denote a hydrogen atom, a branched or linear alkyl group, a halogen atom, an amino, alkylamino, acylamino, ureido or OZ group, Z being a hydroxyalkyl, polyhydroxyalkyl, alkoxyalkyl, mesylaminoalkyl, acylaminoalkyl, ureidoalkyl or carbalkoxyalkyl group.

Other couplers which may be used in the compositions according to the invention are, for example, alpha-naphthol, and heterocyclic compounds derived from benzomorpholine, pyridine, pyrazolones or diketonic compounds. The couplers are used in concentrations of between 0.001 and 5% by weight. Direct dyes may be added to these oxidation dyes in order to impart highlights to the final color.

The soaps used in the compositions according to the invention are preferably present in proportions of between approximately 1 and 25% by weight based on the weight of the composition and preferably between 2 and 20%.

The cationic silicone polymers defined above are used in proportions of between approximately 0.05 and 5% and preferably between 0.1 and 3% by weight based on the total weight of the composition.

The cationic surface-active agents are preferably used in proportions of between approximately 0.05 and 5% by weight based on the weight of the composition.

The cationic polymers are preferably used in proportions of between approximately 0.05 and 5% by weight based on the weight of the composition.

The cationic silicone polymers which are particularly preferred may be introduced into the compositions according to the invention in the form of emulsions containing the silicone polymer as well as nonionic and cationic surface-active agents.

An emulsion of this type which is particularly preferred and used according to the invention consists of the composition sold under the trade name of cationic emulsion "Dow Corning 929" (DC 929) by Dow Corning and which is a combination:

a) of "amodimethicone", defined above b) of trimethylalkyl(tallow)ammonium chloride corresponding to the formula:

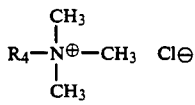

where $R_4$ denotes a mixture of alkenyl and/or alkyl radicals containing 14 to 22 carbon atoms, derived from tallow fatty acids and c) of polyoxyethylenated nonylphenol corresponding to the formula:

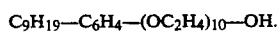

Another emulsion based on cationic silicone polymers according to the present invention is the composition sold under the trade name "Dow Corning Q2 7224" by Dow Corning and which is a combination:

a) of trimethylsilylamodimethicone, defined above b) of polyoxyethylenated octylphenol of the formula:

$C_8H_{17}-C_6H_4-(OCH_2CH_2)_n$ OH where n=40 c) of polyoxyethylenated lauryl alcohol of formula:

$C_{12}H_{25}-(OCH_2-CH_2)_nOH$ where n=6 d) and of glycol.

The dye or beaching agent substrates according to the invention may additionally contain various conventional adjuvants. These adjuvants may be solvents, fatty amides, natural or synthetic fatty alcohols, nonionic or amphoteric surfactants, sequestering agents, antioxidants or perfumes. The substrates or compositions according to the invention may, in particular, contain from 0 to 20% of solvents, from 0 to 15% of fatty amides, from 0 to 25% of fatty alcohols, and from 0 to 25% of nonionic or amphoteric surfactants.

The solvents are chosen from lower aliphatic alcohols such as ethanol, propanol and isopropanol; glycols such as ethylene glycol, propylene glycol, diethylene glycol, dipropylene glycol and hexylene glycol; glycol ethers such as methylglycol, ethylglycol, butylglycol and diethylene glycol monoethyl ether; and aromatic alcohols, especially benzyl alcohol or phenoxyethanol.

Among the fatty amides there may be mentioned lauric, oleic or copra mono- or diethanolamides and stearic monoethanolamide.

These amides are generally used in concentrations from 0.5 to 15% and preferably from 1 to 10% by weight of the total weight. The natural or synthetic fatty alcohols contain from 10 to 18 carbon atoms and are used in concentrations from 1 to 25% and preferably from 5 to 15% by weight of the total weight.

Among the nonionic surfactants there may be mentioned $C_8-C_{18}$ fatty alcohols oxyethylenated with 5 to 30 moles of ethylene oxide, alkylphenols oxyethylenated with 2 to 30 moles of ethylene oxide; and alcohols, 1,2-alkanediols and amides polyglycerolated with 1 to 10 moles of glycerol.

Throughout the preceding text, the concentrations of various constituents are understood to be before dilution of the substrate with the oxidizing agent.

Another subject of the invention is a hair-dyeing composition obtained just before the use by mixing of the substrate specified above, containing the oxidation dye precursors and the reducing agent, with an oxidizing solution which generally consists of hydrogen peroxide.

Another subject of the invention is the composition for lightening and bleaching hair, obtained just before the use by mixing of the substrate defined above with an oxidizing solution which generally consists of hydrogen peroxide and, if desired, persalts such as alkali metal persulphates, perborates and urea peroxide.

One part by weight of the substrate is used with 0.5 to 3 parts by weight of oxidizing agent.

The hair-dyeing or bleaching compositions are applied to hair in sufficient quantity to produce the desired shade or bleaching.

Another subject of the invention is a process for coloring or bleaching hair, which consists in applying to hair a sufficient quantity of a composition containing a substrate such as defined above to which there is added an oxidizing agent chosen from hydrogen peroxide, persalts and a mixture thereof and, if desired, oxidation dye precursors and a reducing agent such as defined above and which is left in contact for a sufficient time to bleach or to dye the hair, after which the latter is rinsed and dried.

The invention will be understood better by means of the examples which follow, without implying any limitation, and in which the parts are expressed on a weight basis.

EXAMPLE 1

| | |
|---|---|
| Oleic acid | 10.4 |
| 98% triethanolamine | 5.44 |
| Mirapol A15 | 0.1 |
| Ceraphyl 60 | 0.1 |
| Cationic emulsion Q.2.7224 | 0.5 |
| 35% strength solution of sodium metabisulphite | 1.3 |
| Pentasodium salt of diethylene-triaminopentaacetic acid | 2.4 |
| Oxidation dyes: | |
| p-phenylenediamine | 0.027 |
| resorcinol | 0.033 |
| meta-aminophenol | 0.030 |
| Hydroquinone | 0.15 |
| 20% aqueous ammonia | 10 |
| Water q.s. | 100 |

At the time of use, 100 g of this composition are diluted with 100 g of 20-volume (6% strength by weight) hydrogen peroxide and are then applied for 30 minutes to blond hair. After rinsing and washing, the hair is dyed to a pearly very light ash-blond shade.

EXAMPLE 2 the procedure is the same as in Example 1. 100 g of composition are diluted with 100 g of 6% weight strength (20-volume) hydrogen peroxide and applied to blond hair for 30 minutes.

| | |
|---|---|
| Oleic acid | 1.3 |
| 98% triethanolamine | 0.68 |
| Mirapol AZI | 0.1 |
| Ceraphyl 60 | 0.1 |
| ABIL 9950 | 0.1 |
| 35% strength solution of sodium metabisulphite | 1.3 |
| Pentasodium salt of diethylene-triaminopentaacetic acid | 2.4 |
| Oxidation dyes: | |
| p-phenylenediamine | 0.03 |
| m-aminophenol | 0.03 |
| Hydroquinone | 0.15 |
| 20% aqueous ammonia | 10 |
| Water q.s. | 100 |
| Shade (on blond hair) | very light blond |

EXAMPLE 3

The procedure is the same as in Example 1. 100 g of composition are diluted with 100 g of 6% weight strength (20-volume) hydrogen peroxide and applied to blond hair for 30 minutes.

| | |
|---|---|
| Oleic acid | 6.94 |
| 98% triethanolamine | 3.63 |
| Lexein CP 125 | 0.1 |
| Alkyldimethylhydroxyethyl-ammonium chloride | 0.1 |
| Cationic emulsion Q.2 7224 | 0.5 |
| 35% strength solution of sodium metabisulphite | 1.3 |
| Pentasodium salt of diethylene- | 2.4 |

| -continued | |
|---|---|
| triaminopentaacetic acid | |
| Oxidation dyes: | |
| p-phenylenediamine | 0.03 |
| resorcinol | 0.03 |
| m-aminophenol | 0.03 |
| Hydroquinone | 0.15 |
| 20% aqueous ammonia | 10 |
| Water q.s. | 100 |

The hair is dyed to a very light blond shade.

EXAMPLE 4

| | |
|---|---|
| Lauric acid | 9.12 |
| 98% triethanolamine | 6.8 |
| Mirapol A15 | 0.1 |
| Catigene CS 40 | 0.1 |
| ABIL 9905 | 0.1 |
| 35% strength solution of sodium metabisulphite | 1.3 |
| Pentasodium salt of diethylenetriaminopentaacetic acid | 2.4 |
| Oxidation dyes: | |
| p-phenylenediamine | 0.8 |
| ortho-aminophenol | 0.3 |
| resorcinol | 0.7 |
| m-aminophenol | 0.04 |
| 2,4-diaminophenoxyethanol | 0.07 |
| Hydroquinone | 0.15 |
| 20% aqueous ammonia | 10 |
| Water q.s. | 100 |

At the time of use, 100 g of this composition are diluted with 70 g of 30-volume hydrogen peroxide. The composition is applied to blond hair for 30 minutes. After rinsing and washing, the hair is dyed to a chestnut brown shade.

EXAMPLES 5 TO 8

The procedure is the same as in Example 1. 100 g of composition are diluted with 100 g of 6% weight strength (20-volume) hydrogen peroxide and applied to blond hair for 30 minutes.

| | EXAMPLES | | | |
|---|---|---|---|---|
| | 5 | 6 | 7 | 8 |
| Lauric acid | 9.12 | 9.12 | 9.12 | 9.12 |
| 8% triethanolamine | 6.8 | 6.8 | 6.8 | 6.8 |
| Mirapol A15 | 0.1 | 0.1 | — | — |
| Lexein CP 125 | — | — | 0.1 | — |
| Cartaretine F8 | — | — | — | 0.1 |
| Ammonyx 4002 | 0.1 | — | — | — |
| Alkyldimethylhydroxyethylammonium chloride | — | 0.1 | — | — |
| Noramium M2 CD (dimethyldilaurylammonium chloride) | — | — | 0.1 | — |
| Arquad 2 HT 75 | — | — | — | 0.1 |
| ABIL 9905 | 0.5 | 0.5 | 0.5 | 0.5 |
| 35% strength solution of sodium metabisulphite | 1.3 | 1.3 | 1.3 | 1.3 |
| Pentasodium salt of diethylenetriaminopentaacetic acid | 2.4 | 2.4 | 2.4 | 2.4 |
| Oxidation dyes: | | | | |
| p-phenylenediamine | 0.44 | 0.48 | 0.03 | 0.03 |
| p-aminophenol | 0.6 | 0.06 | — | — |
| o-aminophenol | — | 0.13 | — | — |
| resorcinol | 0.55 | 0.25 | 0.03 | 0.03 |
| m-aminophenol | 0.12 | 0.08 | 0.03 | 0.03 |
| 1-methyl-2-hydroxy-4-β-hydroxyethylaminobenzene | 0.04 | — | — | — |
| 2,4-diaminophenoxyethanol | 0.05 | 0.06 | — | — |
| Hydroquinone | 0.15 | 0.15 | 0.15 | 0.15 |
| 20% aqueous ammonia | 10 | 10 | 10 | 10 |
| Water q.s. | 100 | 100 | 100 | 100 |
| Shade (on blond hair) | golden chestnut | light chestnut | light blond | very light blond |

EXAMPLES 9 TO 12

The procedure is the same as in Example 1. 100 g of composition are diluted with 100 g of 6% weight strength (20-volume) hydrogen peroxide and applied to blond hair for 30 minutes.

| | EXAMPLES | | | |
|---|---|---|---|---|
| | 9 | 10 | 11 | 12 |
| Oleic acid | 1.6 | 1.6 | 1.58 | 1.58 |
| 2-Amino-2-methyl-1-propanol | 0.5 | 0.5 | — | — |
| N-methylaminoethanol | — | — | 0.42 | 0.42 |
| Mirapol AZI | 0.1 | — | — | — |
| Gafquat 734 | — | 0.1 | 0.1 | 0.1 |
| Ceraphyl 60 | — | — | 0.1 | — |
| Alkyldimethylhydroxyethylammonium chloride | 0.1 | 0.1 | — | — |
| Genamine KDMF | — | — | — | 0.1 |
| Ucar Silicone ALE 56 | — | — | 0.5 | — |
| Cationic emulsion DC 929 | 2 | 2 | — | — |
| ABIL 9905 | — | — | — | 2 |
| 35% strength solution of Na metabisulphite | 1.3 | 1.3 | 1.3 | 1.3 |
| Pentasodium salt of diethylenetriaminopentaacetic acid | 2.4 | 2.4 | 2.4 | 2.4 |
| Oxidation dyes: | | | | |
| p-phenylenediamine | 0.1 | 0.1 | 0.1 | 0.1 |
| p-aminophenol | 0.04 | 0.04 | 0.04 | 0.04 |
| resorcinol | 0.05 | 0.05 | 0.05 | 0.05 |
| m-aminophenol | 0.05 | 0.05 | 0.05 | 0.05 |
| 2,4-diaminophenoxyethanol | 0.01 | 0.01 | 0.01 | 0.01 |
| Hydroquinone | 0.15 | 0.15 | 0.15 | 0.15 |
| 20% aqueous ammonia | 10 | 10 | 10 | 10 |
| Distilled water q.s. | 100 light ash blond | 100 ash blond | 100 pearly light ash blond | 100 light ash blond |

EXAMPLES 13 TO 15

The procedure is the same as in Example 1. 100 g of composition are diluted with 100 g of 6% weight (20-volume) hydrogen peroxide and applied to blond hair for 30 minutes.

| | EXAMPLES | | |
|---|---|---|---|
| | 13 | 14 | 15 |
| Lauric acid | 10.1 | 10.1 | 11.04 |
| 98% triethanolamine | 8.51 | 8.51 | — |
| 2-Amino-2-methyl-1-propanol | — | — | 4.94 |
| Merquat 100 | 2 | — | — |
| Ionene G1 | — | 0.1 | 0.1 |
| Alkyldimethylhydroxyethylammonium chloride | 3 | 3 | 0.1 |
| Ethanol | 11 | 11 | — |
| Propylene glycol | 2 | 2 | — |
| ABIL 9905 | 2.1 | 2.1 | 0.5 |
| 35% strength solution of Na metabisulphite | 1.3 | — | 1.3 |
| Pentasodium salt of diethylenetriaminopentaacetic acid | 2.4 | 2.4 | 2.4 |
| Oxidation dyes: | | | |

-continued

|  | EXAMPLES | | |
| --- | --- | --- | --- |
|  | 13 | 14 | 15 |
| p-phenylenediamine | 0.56 | — | 1.7 |
| p-aminophenol | 0.3 | — | — |
| resorcinol | 0.31 | — | 0.6 |
| m-aminophenol | 0.13 | — | 0.15 |
| o-aminophenol | 0.18 | — | 0.35 |
| 2-methylresorcinol | 0.06 | — | — |
| 2,4-diaminophenoxyethanol | — | — | 0.6 |
| 1-methyl-2-hydroxy-4-N-β-hydroxyethylaminobenzene | 0.03 | — | — |
| Hydroquinone | 0.15 | — | 0.15 |
| 20% aqueous ammonia | 10 | 10.6 | 10 |
| Distilled water q.s. | 100 | 100 | 100 |
| Shade | golden chestnut | lightening | black |

EXAMPLE 16

| Oleic acid | 6.02 |
| --- | --- |
| 2-Amino-2-methyl-1,3-propanediol | 1.98 |
| Lexein QX 3000 | 0.1 |
| Ceraphyl 60 | 0.1 |
| Cationic emulsion Q 27224 | 0.5 |
| 35% strength sodium metabisulphite | 1.3 |
| Pentasodium salt of diethylenetriaminopentaacetic acid | 2.4 |
| Oxidation dyes: | |
| p-Phenylenediamine | 0.44 |
| p-Aminophenol | 0.6 |
| Resorcinol | 0.55 |
| m-Aminophenol | 0.12 |
| 1-Methyl-2-hydroxy-4-β-hydroxyethylaminobenzene | 0.04 |
| 2,4-Diaminophenoxyethanol | 0.05 |
| Hydroquinone | 0.15 |
| 20% aqueous ammonia | 10 |
| Water q.s. | 100 |

100 g of this composition are diluted at the time of use with 100 g of hydrogen peroxide of 6% weight strength. A quantity sufficient to impregnate the hair properly is applied to 90% white hair for 30 minutes and, after rinsing and washing, the hair is dyed to a golden light-chestnut shade.

EXAMPLE 17

| Oleic acid | 6.02 |
| --- | --- |
| 2-Amino-2-methyl-1,3-propanediol | 1.98 |
| Mirapol AD1 | 0.1 |
| Ceraphyl 60 | 0.1 |
| Cationic emulsion Q 27224 | 0.5 |
| 35% strength sodium metabisulphite | 1.3 |
| Pentasodium salt of diethylenetriaminopentaacetic acid | 2.4 |
| Oxidation dyes: | |
| p-Phenylenediamine | 0.44 |
| p-Aminophenol | 0.6 |
| Resorcinol | 0.55 |
| m-Aminophenol | 0.12 |
| 1-Methyl-2-hydroxy-4-β-hydroxyethylaminobenzene | 0.04 |
| 2,4-Diaminophenoxyethanol | 0.05 |
| Hydroquinone | 0.15 |
| 20% aqueous ammonia | 10 |
| Water q.s. | 100 |

100 g of this composition are diluted at the time of use with 100 g of hydrogen peroxide at a concentration of 6% by weight. A sufficient quantity to impregnate the hair properly is applied to 90% white hair for 30 minutes and, after rinsing and washing, the hair is dyed to a golden light-chestnut shade.

EXAMPLE 18

| 98% triethanolamine | 6.80 |
| --- | --- |
| Lauric acid | 9.12 |
| Mirapol A15 | 0.1 |
| Cetylpyridinium chloride | 0.1 |
| ABIL B 9905 | 1 |
| 35% strength sodium metabisulphite | 1.3 |
| Pentasodium salt of diethylenetri-aminopentaacetic acid | 2.4 |
| Oxidation dyes: | |
| p-Phenylenediamine | 0.44 |
| p-Aminophenol | 0.6 |
| Resorcinol | 0.55 |
| m-Aminophenol | 0.12 |
| 1-Methyl-2-hydroxy-4-β-hydroxyethylaminobenzene | 0.04 |
| 2,4-Diaminophenoxyethanol | 0.05 |
| Hydroquinone | 0.15 |
| 20% aqueous ammonia | 10 |
| Water q.s. | 100 |

100 g of this composition are diluted at the time of use with 100 g of hydrogen peroxide at a concentration of 6% by weight. A sufficient quantity to impregnate the hair properly is applied to 90% white hair for 30 minutes and, after rinsing and washing, the hair is of a golden chestnut shade.

Correspondence between trademarks and chemical composition:
ABIL 9905 Cationic polymer of formula:

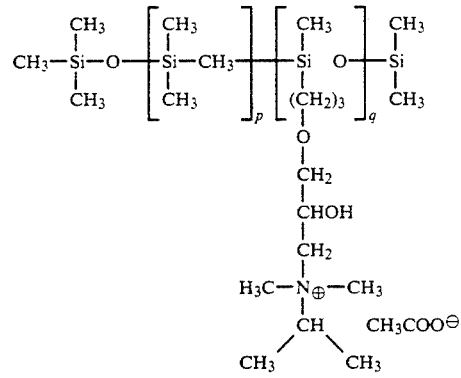

ABIL 9950 Amphoteric silicone polymer of formula:

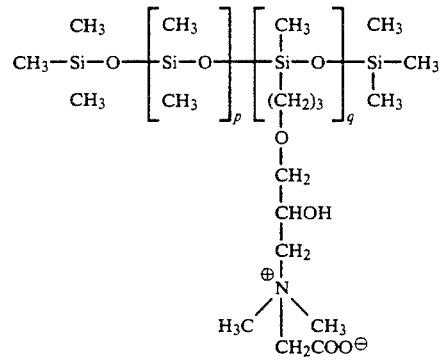

AMMONYX 4001 Dimethylstearylbenzylammonium chloride

ARQUAT 2HT 75 Dimethyldialkyl(hydrogenated tallow)ammonium chloride

CATIGENE CS 40 (Stepan company) Dimethylstearylbenzylammonium chloride

CARTARETINE F8 (Sandoz) Adipic acid/dimethylaminohydroxypropyl/dimethylenetriamine polymer CERAPHYL 60 (Van Dik) Dimethyl-gamma-gluconamidopropylhydroxyethylammonium chloride (cationic surface agent).

CATIONIC EMULSION DC 929 (Dow Corning company) Combination of:
(i) amodimethicone, (ii) tallowtrimonium chloride of formula:

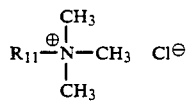

where $R_{11}$ denotes a mixture of $C_{14-22}$ alkenyl and/or alkyl radicals derived from tallow fatty acids;
(iii) NONOXYL 10 of formula:

$$C_9H_{19}-C_6H_4-(OC_2H_4)_{10}-OH$$

CATIONIC EMULSION Q2 7224 (Dow Corning company) Combination of
(a) trimethylsilylamodimethicone
(b) oxtoxynol 40 of formula:

$$C_8H_{17}-C_6H_4-(OCH_2CH_2)_n-OH \text{ where } N=40$$

(c) isolaureth-6 of formula:

$$C_{12}H_{25}(OCH_2CH_2)_n-OH \text{ where } n=6$$

(d) glycol

GAFQUAT 734 (GAF Corporation)
Quaternized copolymer of vinylpyrrolidone and of another copolymerizable monomer (M. W. approximately one million)

GENAMINE KDMF (Hoechst): trimethylalkyl(C-20-22)ammonium chloride

IONENE G1 Quaternary polymer of formula:

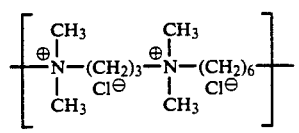

LEXEIN CP 125 (Inolex company) Hydrolysed animal protein substituted by an oleamidopropyldimethylamine radical.

MERQUAT 100 (Merck) Dimethyldialkylammonium chloride homopolymer (M. W. approximately 100,000)

LEXEIN QX 3000 (Inolex) Quaternized animal protein derived from collagen hydrolysates.

MIRAPOL A 15 (Miranol company)
Cationic polymer of formula:

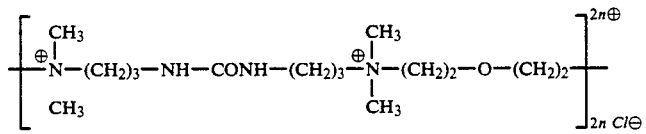

where n is approximately 6

MIRAPOL AZ1 (Miranol company)
Quaternary polyammonium polymer of formula:

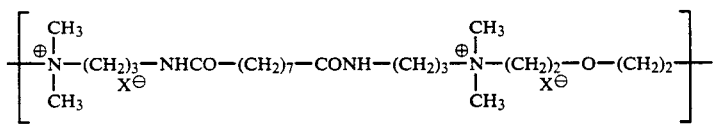

NORAMIUM M2 CD
Dimethyldilaurylammonium chloride UCAR SILICONE ALE 56 (Union Carbide)

Cationic silicone polymer with a flash point of 60° C. according to the ASTM standard D-93, and, at a concentration of 35% of active substance, a viscosity of 11 centipoises at 25° C. and a basicity index of 0.24 milliequivalent/gram.

We claim:

1. A storage stable alkaline cosmetic composition for dyeing or bleaching hair, said composition being dilutable with an oxidizing solution and comprising in an aqueous medium
   (a) at least one fatty acid soap present in an amount ranging from 1 to 25 weight percent based on the total weight of said composition, said fatty acid soap being selected from the group consisting of alkali metal salt of a $C_{12}-C_{18}$ fatty acid containing a saturated or unsaturated fatty chain, an alkanolamine salt of a $C_{12}-C_{18}$ fatty acid containing a saturated or unsaturated fatty chain and mixtures thereof,
   (b) at least one cationic or amphoteric silicone polymer present in an amount ranging from 0.05 to 5 weight percent based on the total weight of said composition, said cationic or amphoteric silicone polymer being selected from the group consisting of (i) a polysiloxane in which at least one silicon atom in the chain carries an aliphatic amino group, and amine group of which is primary, secondary, tertiary or quaternary, (ii) a polysiloxane in which at least one silicon atom in the chain carries an aliphatic amino group, the amine group of which has the betaine structure and (iii) a mixture of (i) and (ii);
   (c) at least one cationic surfactant present in an amount ranging from 0.05 to 5 weight percent based on the total weight of said composition, said cationic surfactant being a compound having the formula

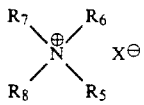

and being selected from the group consisting of
(1) a compound of formula IV wherein $R_5$ and $R_6$ represent methyl and $R_7$ and $R_8$ have the following meanings
  (i) $R_7$ and $R_8$ represent a linear aliphatic radical containing from 12 to 22 carbon atoms, an aliphatic radical derived from tallow fatty acids and containing 14 to 22 carbon atoms, or
  (ii) $R_7$ represents a linear aliphatic radical containing 14–22 carbon atoms and $R_8$ represents methyl or benzyl, or
  (iii) $R_7$ represents an alkylamidopropyl radical wherein the alkyl moiety has 14–22 carbon atoms and $R_8$ represents an alkylacetate group wherein the alkyl moiety has 12–16 carbon atoms, or
  (iv) $R_7$ represents a gamma-gluconamidopropyl radical, an aliphatic radical derived from tallow fatty acids or a $C_{16}$-$C_{18}$ alkyl radical, and $R_8$ represents hydroxyethyl, and
$X^\ominus$ represents an anion,
(2) a compound of formula IV wherein
$R_5$ represents alkylamidoethyl, alkenylamidoethyl or a mixture thereof, said alkyl moiety containing 14–22 carbon atoms and originating from tallow fatty acids and said alkenyl moiety containing 14–22 carbon atoms and originating from tallow fatty acids, and
$R_6$ and $R_7$ together with the nitrogen atom to which they are attached form a 2-alkyl-4,5-dihydroimidazole heterocycle ring wherein the alkyl moiety is derived from tallow fatty acids,
$R_8$ represents methyl and
$X^\ominus$ represents a methosulphate ion, and
(3) a compound of formula IV wherein $R_5$, $R_6$, and $R_7$ form with the nitrogen atom to which they are attached a six membered aromatic heterocyclic ring,
$R_8$ represents a $C_{14}$-$C_{18}$ alkyl radical and
$X^\ominus$ represents a halide anion;
(d) at least one alkalizing agent present in an amount sufficient such that the pH of said composition is higher than 7, said alkalizing agent being selected from sodium hydroxide, potassium hydroxide, aqueous ammonia and an alkanolamine;
(e) at least one cationic polymer present in an amount ranging from 0.05 to 5 weight percent based on the total weight of said composition, said cationic polymer being selected from the group consisting of:
(1) a quaternary polyammonium polymer selected from the group consisting of (a) a polymer consisting of repeating units of the formula

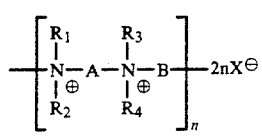

wherein
(i) $R_1$, $R_2$, $R_3$ and $R_4$, each independently, represent an aliphatic, alicyclic or arylaliphatic radical containing 1–20 carbon atoms or a $C_1$-$C_6$ hydroxyaliphatic radical, or
(ii) $R_1$ and $R_2$ and $R_3$ and $R_4$, together or separately, form with the nitrogen atoms to which they are attached a heterocyclic ring or a heterocyclic ring containing a second heteroatom other than nitrogen, or
(iii) $R_1$, $R_2$, $R_3$ and $R_4$ represent a linear or branched $C_2$-$C_6$ alkyl group substituted by a nitrile group, an ester group, an acyl group, an amide group, a group of the formula

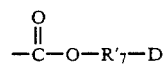

or a group of the formula

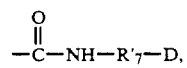

wherein $R'_7$ represents alkylene and D represents a quaternary ammonium group,
A and B represent a linear or branched, saturated or unsaturated polymethylene group containing 2 to 20 carbon atoms or a linear or branched saturated or unsaturated polymethylene group containing 2 to 20 carbon atoms and containing in the main chain one or more of an aromatic ring, an oxygen atom, a sulphur atom, a sulphoxide group, a sulphone group, a disulphide group, an amine group, an alkylamine group, a quaternary ammonium group, a hydroxyl group, a ureido group, an amide group or an ester group, or
A and $R_1$ and $R_3$ together with the two nitrogen atoms to which they are attached form a piperazine ring,
$X^\ominus$ is an anion derived from an inorganic or organic acid, and
n is such that the molecular weight of the polymer ranges from 1,000 to 100,000 and
(b) a polymer consisting of repeating units of the formula

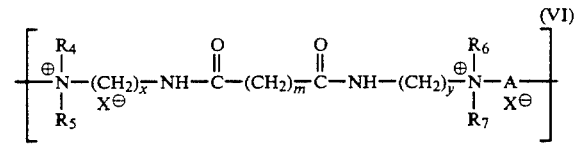

wherein
$R_4$, $R_5$, $R_6$ and $R_7$, each independently represent hydrogen, methyl, ethyl, propyl, 2-hydroxyethyl, 2-hydroxypropyl, or —$CH_2$—$CH_2$—(O—$CH_2$—$CH_2$)$_p$—OH wherein p is 0 or an integer ranging from 1 to 6, with the proviso that $R_4$, $R_5$, $R_6$ and $R_7$ do not simultaneously represent hydrogen,
x and y, each independently, represent integers ranging from 1 to 6,
m is 0 or an integer ranging from 1 to 34,
X is a halogen atom, and
A is a divalent group having the formula, —$CH_2$—$CH_2$—O—$CH_2$—$CH_2$—;
(2) a vinylpyrrolidone/dialkylaminoalkyl acrylate quaternized or not;

(3) a vinylpyrrolidone/dialkylaminoalkyl methacrylate quaternized or not;

(4) poly (methacrylamidopropyltrimethyl ammonium chloride);

(5) a cationic protein which is a chemically modified polypeptide bearing amine or quaternary ammonium groups at the end of the chain or grafted onto the chain;

(6) a polyaminoamide selected from the group consisting of (i) a water soluble polyaminoamide obtained by condensation of an acidic compound with a polyamine, (ii) a crosslinked water soluble polyaminoamide obtained by condensation of an acidic compound with a polyamine, (iii) an alkylated water soluble polyaminoamide obtained by condensation of an acidic compound with a polyamine, (iv) a polyaminoamide resulting from the condensation of a polyalkylenepolyamine with a polycarboxylic acid and alkylated with a difunctional agent, and (v) a polyaminoamide obtained by reacting a polyalkylenepolyamine comprising two primary amine groups and at least one secondary amine group with a dicarboxylic acid, the molar ratio between the said polyalkylenepolyamine and the said dicarboxylic acid being between 0.8/1 and 1.4/1, the resulting polyaminoamide being reacted with epichlorohydrin, the molar ration of epichlorohydrin to the secondary amine groups of the polyaminoamide being between 0.5/1 and 1.8/1;

a crosslinked polyaminoamide;
an alkylated polyaminoamide; and
mixtures thereof.

2. A storage stable, alkaline cosmetic composition for dyeing hair, said composition being dilutable with an oxidizing solution and comprising in an aqueous medium (a) at least one fatty acid soap present in an amount ranging from 1 to 25 weight percent based on the total weight of said composition, said fatty acid soap being selected from the group consisting of alkali metal salt of a $C_{12}$-$C_{18}$ fatty acid containing a saturated or unsaturated fatty chain, an alkanolamine salt of a $C_{12}$-$C_{18}$ fatty acid containing a saturated or unsaturated fatty chain and mixtures thereof, (b) at least one cationic or amphoteric silicone polymer present in an amount ranging from 0.05 to 5 weight percent based on the total weight of said composition, said cationic or amphoteric silicone polymer being selected from the group consisting of (i) a polysiloxane in which at least one silicon atom in the chain carries an aliphatic amino group, the amine group of which is primary, secondary, tertiary or quaternary, (ii) a polysiloxane in which at least one silicon atom in the chain carries an aliphatic amino group, the amine group of which has the betaine structure and (iii) a mixture of (i) and (ii);

(c) at least one cationic surfactant present in an amount ranging from 0.05 to 5 weight percent based on the total weight of said composition, said cationic surfactant being a compound having the formula

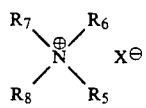

and being selected from the group consisting of (1) a compound of formula IV wherein $R_5$ and $R_6$ represent methyl and $R_7$ and $R_8$ have the following meanings (i) $R_7$ and $R_8$ represent a linear aliphatic radical containing from 12 to 22 carbon atoms, an aliphatic radical derived from tallow fatty acids and containing 14 to 22 carbon atoms, or (ii) $R_7$ represents a linear aliphatic radical containing 14–22 carbon atoms and $R_8$ represents methyl or benzyl, or (iii) $R_7$ represents an alkylamidopropyl radical wherein the alkyl moiety has 14–22 carbon atoms and $R_8$ represents an alkylacetate group wherein the alkyl moiety has 12–16 carbon atoms, or (iv) $R_7$ represents a gamma-gluconamidopropyl radical, an aliphatic radical derived from tallow fatty acids or a $C_{16}$-$C_{18}$ alkyl radical, and $R_8$ represents hydroxyethyl, and $X^{\ominus}$ represents an anion, (2) a compound of formula IV wherein $R_5$ represents alkylamidoethyl, alkenylamidoethyl or a mixture thereof, said alkyl moiety containing 14–22 carbon atoms and originating from tallow fatty acids and said alkenyl moiety containing 14–22 carbon atoms and originating from tallow fatty acids, and $R_6$ and $R_7$ together with the nitrogen atom to which they are attached form a 2-alkyl-4,5-dihydroimidazole heterocycle ring wherein the alkyl moiety is derived from tallow fatty acids, $R_8$ represents methyl and $x^{\ominus}$ represents a methosulphate ion, and (3) a compound of formula IV wherein $R_5$, $R_6$, and $R_7$ form with the nitrogen atom to which they are attached a six membered aromatic heterocyclic ring, $R_8$ represents a $C_{14}$-$C_{18}$ alkyl radical and $X^{\ominus}$ represents a halide anion;

(d) at least one alkalizing agent present in an amount sufficient such that the pH of said composition is higher than 7, said alkalizing agent being selected from sodium hydroxide, potassium hydroxide, aqueous ammonia and an alkanolamine;

(e) at least one cationic polymer present in an amount ranging from 0.05 to 5 percent based on the total weight of said composition, said cationic polymer being selected from the group consisting of:

(1) a quaternary polyammonium polymer selected from the group consisting of (a) a polymer consisting of repeating units of the formula

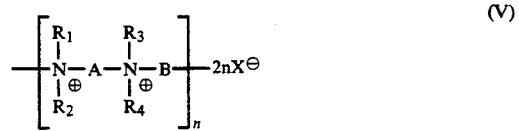

wherein (i) $R_1$, $R_2$, $R_3$ and $R_4$, each independently, represent an aliphatic, alicyclic or arylaliphatic radical containing 1-20 carbon atoms or a $C_1$-$C_6$ hydroxyaliphatic radical, or (ii) $R_1$ and $R_2$ and $R_3$ and $R_4$, together or separately, form with the nitrogen atoms to which they are attached a heterocyclic ring or a heterocyclic ring containing a second heteroatom other than nitrogen, or (iii) $R_1$, $R_2$, $R_3$ and $R_4$ represent a linear or branched $C_2$-$C_6$ alkyl group substituted by a nitrile group, an ester group, an acyl group, an amide group, a group of the formula

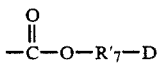

or a group of the formula

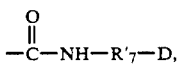

wherein $R'_7$ represents alkylene and D represents a quaternary ammonium group, A and B represent a linear or branched, saturated or unsaturated polymethylene group containing 2 to 20 carbon atoms or a linear or branched saturated or unsaturated polymethylene group containing 2 to 20 carbon atoms and containing in the main chain one or more of an aromatic ring, an oxygen atom, a sulphur atom, a sulphoxide group, a sulphone group, a disulphide group, an amine group, an alkylamine group, a quaternary ammonium group, a hydroxyl group, a ureido group, an amide group or an ester group, or A and $R_1$ and $R_3$ together with the two nitrogen atoms to which they are attached form a piperazine ring, $X^\ominus$ is an anion derived from an inorganic or organic acid, and n is such that the molecular weight of the polymer ranges from 1,000 to 100,000 and (b) a polymer consisting of repeating units of the formula

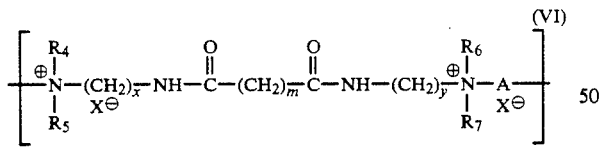

wherein
$R_4$, $R_5$, $R_6$ and $R_7$, each independently represent hydrogen, methyl, ethyl, propyl, 2-hydroxyethyl, 2-hydroxypropyl, or —$CH_2$—$CH_2$—(O—$CH_2$—$CH_2$)$_p$—OH wherein p is 0 or an integer ranging from 1 to 6, with the proviso that $R_4$, $R_5$, $R_6$ and $R_7$ do not simultaneously represent hydrogen, x and y, each independently, represent integers ranging from 1 to 6, m is 0 or an integer ranging from 1 to 34, X is a halogen atom, and A is a divalent group having the formula, —$CH_2$—$CH_2$—O—$CH_2$—$CH_2$—;

(2) a vinylpyrrolidone/dialkylaminoalkyl acrylate quaternized or not;

(3) a vinylpyrrolidone/dialkylaminoalkyl methacrylate quaternized or not;

(4) poly (methacrylamidopropyltrimethyl ammonium chloride);

(5) a cationic protein which is a chemically modified polypeptide bearing amine or quaternary ammonium groups at the end of the chain or grafted onto the chain;

(6) a polyaminoamide selected from the group consisting of (i) a water soluble polyaminoamide obtained by condensation of an acidic compound with a polyamine, (ii) a crosslinked water soluble polyaminoamide obtained by condensation of an acidic compound with a polyamine, (iii) an alkylated water soluble polyaminoamide obtained by condensation of an acidic compound with a polyamine, (iv) a polyaminoamide resulting from the condensation of a polyalkylenepolyamine with a polycarboxylic acid and alkylated with a difunctional agent, and (v) a polyaminoamide obtained by reacting a polyalkylenepolyamine comprising two primary amine groups and at least one secondary amine group with a dicarboxylic acid, the molar ratio between the said polyalkylenepolyamine and the said dicarboxylic acid being between 0.8/1 and 1.4/1, the resulting polyaminoamide being reacted with epichlorohydrin, the molar ratio of epichlorohydrin to the secondary amine groups of the polyaminoamide being between 0.5/1 and 1.8/1;

a crosslinked polyaminoamide;

an alkylated polyaminoamide;

a cationic cyclopolymer selected from the group consisting of (i) a cationic cyclopolymer consisting of repeating units of the formula

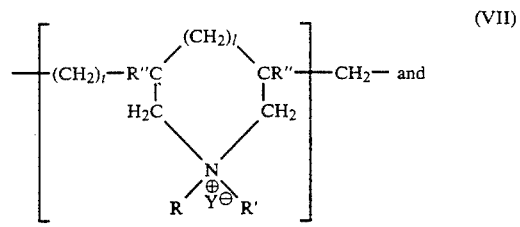

(ii) a cationic cyclopolymer consisting of repeating units of the formula

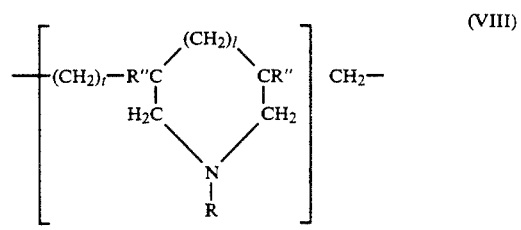

wherein
l and t are equal to 0 and 1 and the sum of l+t is equal to 1,

R" represents hydrogen or methyl,

R and R', each independently, represent alkyl containing 1-22 carbon atoms, hydroxyalkyl containing 1-5 carbon atoms or lower amidoalkyl, or R and R' together with the nitrogen atom to which they are attached form a piperidyl or morpholinyl group, and mixtures thereof, (f) an oxidation dye precursor in an amount effective to dye the hair and (g) 0.5 to 2 percent by weight of a reducing agent.

3. The cosmetic composition of claim 1 wherein said fatty acid soap is present in an amount ranging from 2 to 20 weight percent based on the total weight of said composition.

4. The cosmetic composition of claim 1 wherein said cationic silicone polymer is selected from the group consisting of (i) a polymer having the formula

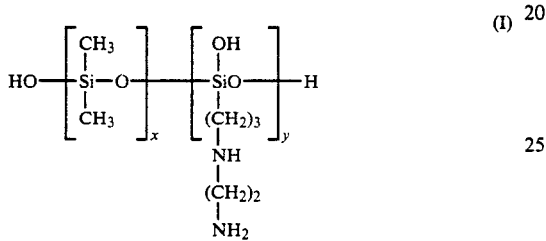
(I)

wherein x is 4 or more and y is such that the resulting polymer has an average molecular weight ranging approximately between 5,000 and 10,000, (ii) a polymer of the formula $$(R_1)_a G_{3-a}—Si(OSiG_2)_n[OSiG_b(R_1)_{2-b}]_m$$
$$O—SiG_{3-a}(R_1)_a \quad (II)$$

wherein

G is selected from the group consisting of hydrogen, phenyl, OH, $C_1$-$C_8$ alkyl, a represents 0 or an integer ranging from 1 to 3, b represents 0 or 1, the sum of n+m is a number ranging from 1 to 2,000, n representing a number ranging from 0 to 1,999 and m representing an integer ranging from 1 to 2,000, $R_1$ is a monovalent radical having the formula $C_qH_{2q}L$ wherein q is an integer ranging from 2 to 8 and L is selected from the group consisting of $N(R_2)CH_2—CH_2—N(R_2)_2$, $N(R_2)_2$, $^{\oplus}N(R_2)_3A^{\ominus}$, $^{\oplus}N(R_2)H_2A^{\ominus}$ and $N(R_2)CH_2—CH_2—^{\oplus}NR_2H_2A^{\ominus}$ wherein $R_2$ is selected from the group consisting of hydrogen, phenyl, benzyl and alkyl containing 1-20 carbon atoms, and $A^{\ominus}$ represents a halide atom, (iii) a polymer having the formula

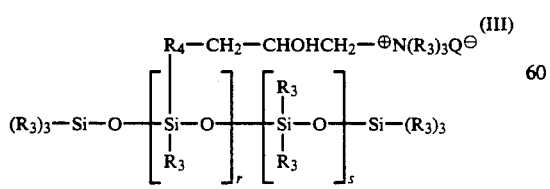
(III)

wherein $R_3$ represents a monovalent hydrocarbon radical containing 1-18 carbon atoms, $R_4$ represents a $C_1$-$C_{18}$ alkylene radical or a $C_1$-$C_{18}$ alkyleneoxy radical, $Q^{\ominus}$ is a halide ion, r represents a statistical average value of 2 to 20, s represents a statistical average value of 20 to 200, and (iv) a polymer of the formula

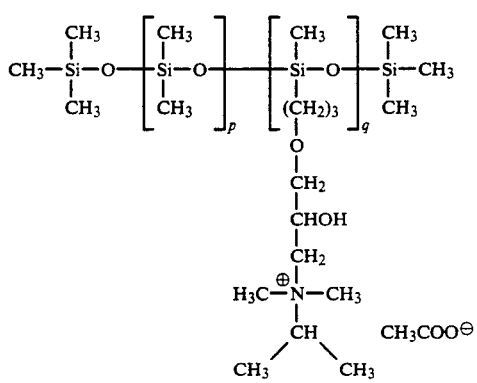

wherein p and q are integers which depends on the molecular weight of the polymer, the average molecular weight of the polymer ranging from 1,000 to 8,000.

5. The cosmetic composition of claim 4 where in said polymer (ii) a is 0.

6. The cosmetic composition of claim 4 where in said polymer (ii) b is 1.

7. The cosmetic composition of claim 4 where in said polymer (ii) the sum n+m ranges from 50 to 150 wherein n represents a number ranging from 49 to 149 and m represents a number ranging from 1 to 10.

8. The cosmetic composition of claim 4 where in said polymer (iii) r has a statistical average value ranging from 2 to 8.

9. The cosmetic composition of claim 4 where in said polymer (iii) s has a statistical average value ranging from 20 to 50.

10. The cosmetic composition of claim 1 wherein said amphoteric silicone polymer has the formula

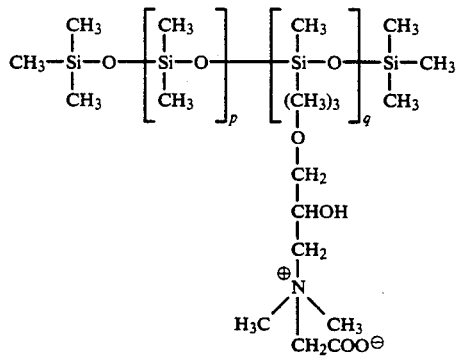

wherein p and q are integers which depend on the molecular weight of the polymer, the average molecular weight of the polymer ranging from 1,000 to 8,000.

11. The cosmetic composition of claim 1 wherein said silicone polymer has the formula

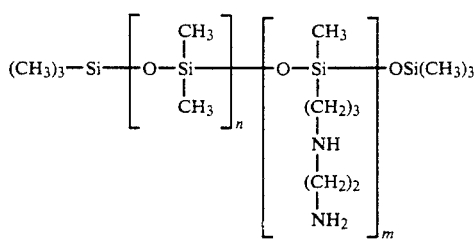

wherein the sum of n+m represents a number ranging from 1 to 2,000, n representing a number ranging from 1 to 1,999, and m representing a number ranging from 1 to 2,000.

12. The cosmetic composition of claim 1 wherein said silicone polymer is an emulsion of a dimethyl polysiloxane modified by the incorporation of bis-silyl groups of the formula —OSi—C$_3$H$_6$NH—C$_3$H$_6$ SiO—.

13. The cosmetic composition of claim 1 wherein said silicone polymer is present in an amount ranging from 0.1 to 3 weight percent based on the total weight of said composition.

14. The cosmetic composition of claim 1 wherein said cationic surface agent is selected from the group consisting of
  (i) dimethyldilaurylammonium chloride,
  (ii) dimethyldialkylammonium chloride wherein the alkyl moiety is derived from hydrogenated tallow,
  (iii) dimethyldialkylammonium chloride wherein the alkyl moiety has 18 carbon atoms,
  (iv) trimethylalkylammonium chloride wherein the alkyl moiety has 20-22 carbon atoms,
  (v) cetylpyridinium chloride,
  (vi) dimethyldialkylammonium chloride wherein the alkyl moiety has 12-14 carbon atoms,
  (vii) dimethyl-gamma-gluconamidopropyl-hydroxyethylammonium chloride,
  (viii) dimethyldicetylammonium chloride;
  (ix) dimethylhydroxyethylalkyl ammonium chloride wherein the alkyl moiety is derived from tallow,
  (x) dimethylhydroxyethylcetylammonium chloride,
  (xi) dimethylstearylbenzylammonium chloride, and
  (xii) mixtures of (i)–(xi).

15. The cosmetic composition of claim 1 wherein said alkanolamine is monoethanolamine, diethanolamine, triethanolamine, 2-amino-2-methyl-1-propanol, 2-amino-2-methyl-1,3-propanediol and triisopropanolamine.

16. The cosmetic composition of claim 1 wherein said quaternary polyammonium polymer is selected from the group consisting of (1) a polymer consisting of repeating units of the formula

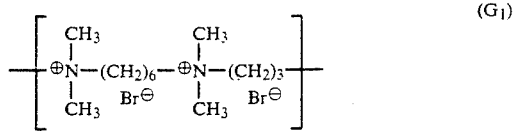

(2) a polymer consisting of repeating units of the formula

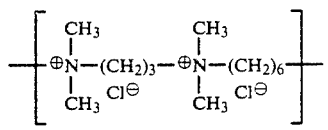

(3) a polymer consisting of repeating units of the formula

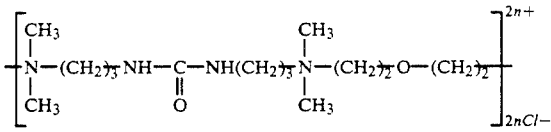

wherein n is equal to approximately 6,
(4) a polymer consisting of repeating units of the formula

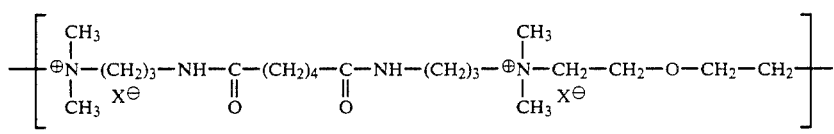

wherein X represents halogen,
(5) a polymer consisting of repeating units of the formula

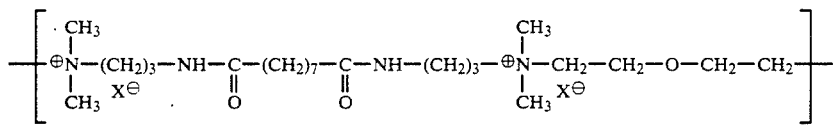

wherein X represents halogen, and
(6) poly(dimethylbutenylammonium chloride)-α-ω-bis (triethanolammonium chloride).

17. The cosmetic composition of claim 1 wherein said cationic protein is selected from the group consisting of
  (1) a collagen hydrolysate bearing a triethylammonium group,
  (2) a collagen hydrolysate bearing a trimethylammonium chloride group or a trimethylstearylammonium chloride group,
  (3) an animal protein hydrolysate bearing a trimethylbenzylammonium group,
  (4) a protein hydrolysate bearing, on the polypeptide chain, a quaternary ammonium group comprising at least one alkyl radical containing 1-18 carbon atoms and having an average molecular weight ranging from approximately 2,500 to 12,000,
  (5) a protein of the formula

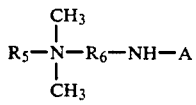

wherein

A represents a protein residue derived from a collagen protein hydrolysate, $R_5$ represents a lipophilic group containing up to 30 carbon atoms, and $R_6$ represents alkylene containing 1-6 carbon atoms, said protein having a molecular weight ranging from 1,500 to 10,000, and (6) an animal protein hydrolysate bearing a dimethylamine group.

18. The cosmetic composition of claim 17 wherein said cationic protein is selected from the group consisting of (1) a protein hydrolysate having on the polypeptide chain thereof, a quaternary ammonium group containing a $C_{12}$ alkyl group and having an average molecular weight of approximately 2,500, (2) a protein hydrolysate whose polypeptide chain has an average molecular weight of approximately 2,500 and whose quaternary ammonium group contains a $C_{10}$-$C_{18}$ alkyl group, (3) a protein hydrolysate whose polypeptide chain has an average molecular weight of approximately 2,700 and whose quaternary ammonium group contains a $C_{18}$ alkyl group, (4) a protein hydrolysate whose polypeptide chain has an average molecular weight of order of 12,000 and whose quaternary ammonium group contains an alkyl group containing from 1-18 carbon atoms, and (5) a protein of the formula

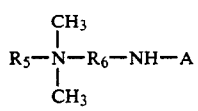

wherein A, $R_5$ and $R_6$ are as defined in claim 46 and which has a molecular weight between 2,000 and 5,000.

19. The cosmetic composition of claim 18 wherein said cationic copolymer is selected from the group consisting of
(i) homopolymer of dimethyldiallylammonium chloride having a molecular weight less than 100,000 and
(ii) copolymer of dimethyldiallylammonium chloride and acrylamide having a molecular weight greater than 500,000.

20. The cosmetic composition of claim 1 wherein said reducing agent is selected from the group consisting of thioglycolic acid, thiolactic acid, ammonium thiolactate and sodium metabisulfite, said reducing agent being present in an amount ranging from 0.5 to 2 percent by weight based on the total weight of said composition.

21. The cosmetic composition of claim 1 wherein said oxidation dye precursor is
(i) an oxidation base selected from the group consisting of a diamine, a monoaminophenol and a diaminophenol, or (ii) a modifier or coupler selected from the group consisting of a meta-diamine, a meta-aminophenol, a phenol and a polyphenol, or
(iii) a mixture of (i) and (ii).

22. The cosmetic composition of claim 21 wherein said oxidation base is selected from the group consisting of
(i) a compound of the formula

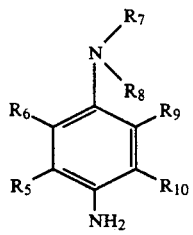

wherein $R_7$ and $R_8$ each independently represent hydrogen, straight or branched chain lower alkyl, monohydroxylated alkyl, polyhydroxylated alkyl, piperidinoalkyl, carbamylalkyl, dialkylcarbamylalkyl, aminoalkyl, monoalkylaminoalkyl, dialkylaminoalkyl, ω-aminosulphonylalkyl, carboxyalkyl, alkylsulphonamidoalkyl, arylsulphonamidoalkyl, morpholinoalkyl, acylaminoalkyl, sulphoalkyl or alkoxyalkyl, wherein the alkyl moiety of each contains 1-4 carbon atoms, or $R_7$ and $R_8$ together with the nitrogen atom to which they are attached form a morpholinyl or piperidinyl group, $R_5$, $R_6$, $R_9$ and $R_{10}$ each independently represent hydrogen, halogen, lower alkyl containing 1-4 carbon atoms or OZ wherein Z represents hydroxyalkyl, alkoxyalkyl, acylamino alkyl, carbalkoxyaminoalkyl, mesylaminoalkyl, ureidoalkyl, aminoalkyl, monoalkylaminoalkyl or dialkylaminoalkyl, and the hydrochloride, hydrobromide, sulphate or tartrate thereof, (ii) p-aminophenol and the homologue thereof whose aromatic nucleus is substituted by methyl or chlorine,
(iii) N-methyl-p-aminophenol,
(iv) heterocyclic derivative of pyridine,
(v) heterocyclic derivative of benzomorpholine,
(vi) 5-aminoindole,
(vii) orthoaminophenol,
(viii) p-aminodiphenylamine and
(ix) ortho-phenylenediamine
said oxidation base being present in an amount ranging from 0.01 to 5 weight percent based on the total weight of said composition.

23. The cosmetic composition of claim 21 which also contains at least one coupler selected from the group consisting of
(i) a compound of the formula

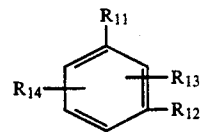

wherein $R_{11}$ and $R_{12}$ each independently represent hydroxyl or -NHR wherein R represents hydrogen, acyl, ureido, carbalkoxy, carbamylalkyl, alkyl, dialkylcarbamylalkyl, hydroxyalkyl or mesylaminoalkyl, or $R_{11}$ and $R_{12}$ represent hydrogen, alkoxy or alkyl with the proviso that at least one of $R_{11}$ and $R_{12}$ represents OH, $R_{13}$ and $R_{14}$ represent hydrogen, branched or linear alkyl, halogen, amino, alkylamino, acylamino, ureido or OZ wherein Z represents hydroxyalkyl, polyhydroxyalkyl, aikoxylalkyl, mesylaminoalkyl, acylaminoalkyl, ureidoalkyl or carbalkoxyalkyl, (ii) α-naphthol, and (iii) heterocyclic compound derived from benzomorpholine, pyridine, pyrazolone and a diketone compound, said coupler being present in an amount ranging from 0.001 to 5 weight percent based on the total weight of said composition.

24. The cosmetic composition of claim 1 wherein said cationic silicone polymer is present in the form of an emulsion that also contains a nonionic or cationic surface active agent, said emulsion being selected from the group consisting of (i) an emulsion which is a combination of
(a) a polymer having the formula

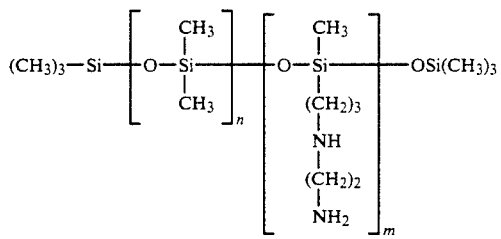

wherein the sum or m+n is a number ranging from 1 to 2,000, n representing a number ranging from 0 to 1,999 and m representing a number ranging from 1 to 2,000, (b) polyoxyethylenated octylphenol having the formula $C_8H_{17}-C_6H_4-(OCH_2CH_2)_n-OH$ wherein n is 40 and (c) polyoxyethylenated laurylalcohol or the formula $C_{12}H_{25}-(OCH_2CH_2)_n-OH$ wherein n is 6, (d) glycol, and (ii) an emulsion which is a combination of silicone polymer having the formula

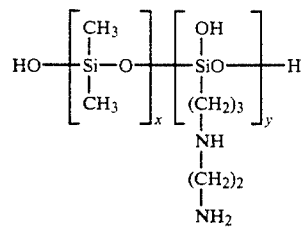

(I)

wherein x is 4 or more and y is such that the resulting polymer has an average molecular weight ranging between 5,000 and 10,000, (b) trimethylalkyl ammonium chloride wherein the alkyl moiety is derived from tallow and having the formula

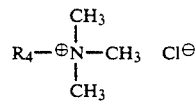

wherein $R_4$ represents a mixture of alkenyl radicals, a mixture of alkyl radicals or a mixture of alkyl and alkenyl radicals containing 14-22 carbon atoms and being derived from tallow fatty acids and (c) polyoxyethylenated nonylphenol having the formula $C_9H_{19}-C_6H_4-(OC_2H_4)_{10}-OH$.

25. The cosmetic composition of claim 1 which also includes at least one of a solvent, a fatty amide, a fatty alcohol, a nonionic surface agent, an amphoteric surface agent, a sequestering agent and a perfume.

26. A process for bleaching hair comprising applying to the hair in an amount effective to bleach said hair a hair bleaching formulation comprising an admixture of the cosmetic composition of claim 1 and 0.5 to 3 parts of the weight thereof of an oxidizing agent selected from the group consisting of hydrogen peroxide, a persalt and a mixture thereof, permitting said hair bleaching formulation to remain in contact with the hair for a time sufficient to bleach said hair, rinsing the hair with water and drying said hair.

27. A process for dyeing hair comprising applying to the hair in an amount effective to dye the hair a hair dyeing formulation comprising an admixture of the cosmetic composition of claim 1 and 0.5 to 3 parts of the weight thereof of an oxidizing agent selected from the group consisting of hydrogen peroxide, a persalt and a mixture thereof, permitting said hair dyeing formulation to remain in contact with the hair for a time sufficient to dye said hair, rinsing the hair and drying the hair.

* * * * *